United States Patent [19]

Trius Oliva et al.

[11] Patent Number: 5,576,451
[45] Date of Patent: Nov. 19, 1996

[54] ESTERS OF FATTY ACIDS WITH ETHOXYLATED POLYOLS

[75] Inventors: Antonio Trius Oliva, Valldoreix; Oriol Ponsati Obiols, Barcelona; Joaquim Bigorra Llosas, Sabadell; Esther Prat Queralt, Alella, all of Spain

[73] Assignee: Henkel Kommanditgesellschaft auf Aktien, Duesseldorf, Germany

[21] Appl. No.: 244,066

[22] PCT Filed: Nov. 4, 1992

[86] PCT No.: PCT/EP92/02525

§ 371 Date: May 13, 1994

§ 102(e) Date: May 13, 1994

[87] PCT Pub. No.: WO93/10072

PCT Pub. Date: May 27, 1993

[30] Foreign Application Priority Data

Nov. 13, 1991 [DE] Germany ............... 41 37 317.0

[51] Int. Cl.$^6$ .................................. C07C 59/00
[52] U.S. Cl. ............... 554/227; 554/149; 554/213; 554/219; 252/351
[58] Field of Search ............... 554/149, 227; 252/351

[56] References Cited

U.S. PATENT DOCUMENTS

| | | | |
|---|---|---|---|
| 4,614,622 | 9/1986 | Huettinger et al. | 240/410.7 |
| 5,034,159 | 7/1991 | Tesmann et al. | 252/551 |
| 5,292,910 | 3/1994 | Raths et al. | 554/149 |

FOREIGN PATENT DOCUMENTS

| | | |
|---|---|---|
| 0343463 | 11/1989 | European Pat. Off. . |
| 0356255 | 2/1990 | European Pat. Off. . |
| 2534923 | 4/1984 | France . |
| 3541813 | 6/1987 | Germany . |
| 1535 | 6/1987 | Germany . |
| 3600263 | 7/1987 | Germany . |
| 3730179 | 3/1989 | Germany . |
| 3843713 | 11/1989 | Germany . |
| 4010606 | 10/1991 | Germany . |
| 9005714 | 5/1990 | WIPO . |

OTHER PUBLICATIONS

Seifen–Öle–Fette–Wachse 116 Jg.—Nr., Feb. 1990.
Seifen–Öle–Fette—Wachse 113 Jg.—Nr. May 1987.
*Cosmetics & Toiletries,* 103, Dec. 1988, pp. 99–129, Lochhead, R.
J. Falbe (ed., "Surfactants in Consumer Products", Springer Verlag, Berlin, 1986, pp. 54–85 (not available).

*Primary Examiner*—Gary Geist
*Assistant Examiner*—Deborah D. Carr
*Attorney, Agent, or Firm*—Wayne C. Jaeschke; Norvell E. Wisdom, Jr.; John S. Child, Jr.

[57] ABSTRACT

Esters of fatty acids with ethoxylated polyols are prepared by (a) ethoxylating polyols in the presence of basic catalysts at high temperatures with 80 to 150 moles ethylene oxide per mol polyol and then (b) reacting the reaction product with 1 to 1.3 moles fatty acids per mole of hydroxyl groups contained in the original polyol, in the presence of acid catalysts. These esters are useful as thickeners of aqueous solutions of surface active agents.

20 Claims, No Drawings

ESTERS OF FATTY ACIDS WITH ETHOXYLATED POLYOLS

This application is a 371 of PCT/EP92/02525 filed Nov. 4, 1992.

FIELD OF THE INVENTION

This invention relates to esters of fatty acids with ethoxylated polyols, to a process for their production and to their use as thickeners for aqueous surfactant solutions.

PRIOR ART

Aqueous surfactant solutions, more particularly those used in the field of personal hygiene as hair shampoos, foam baths, shower baths, hand washing pastes and the like, generally contain anionic or amphoteric surfactants, for example of the fatty alcohol ether sulfate, alkanesulfonate, sulfosuccinate, ether carboxylic acid or betaine types, as their surfactant components. To stabilize these clear or disperse systems and to improve their flow behavior to such an extent that they are easy to dispense, thickeners are normally added to the surfactant solutions [Seifen-Öle-Fette-Wachse {Title in English: Soaps-Oils-Fats-Waxes}, 116, 60 (1990)].

Several inorganic and organic substances which are suitable for increasing the viscosity of aqueous surfactant solutions are known to the expert for this purpose.

A number of water-soluble salts, for example sodium chloride, may be used as inorganic thickeners [Seifen-Öle-Fette-Wachse, 113, 135 (1987)].

Known organic thickeners include, for example, polyethylene glycol difatty acid esters [DE 35 41 813 A1, DE 35 51 535 A1, DE 36 00 263 A1], glycerol trifatty acid esters [Cosm. Toil., 103, 99 (1988)], ethoxylated fatty alcohols [DE 37 30 179 A1, EP 0 343 463 A2], water-soluble polymers and fatty acid alkanolamides.

In most cases, the required viscosity cannot be built up in the surfactant solution simply by using anionic salts. In those cases where this is possible, the anionic salts have to be used in high concentrations. Accordingly, organic thickeners generally have to be used in addition to the inorganic salts; this involves a number of disadvantages. Thus, solutions thickened with polyethylene glycol fatty acid diesters, glycerol trifatty acid esters or fatty alcohol ethoxylates often show inadequate viscosity stability in storage, while water-soluble polymers are often poorly soluble and show unwanted, slimy flow behavior with a tendency to become stringy.

By virtue of their excellent thickening effect, particular significance has long been attributed to fatty acid alkanolamides. On account of a small production-related content of free alkanolamines, which can give rise to the formation of nitrosamines, these substances are limited in their suitability for use in cosmetic products. The same also applies to virtually all other nitrogen-containing thickeners.

Accordingly, the problem addressed by the present invention was to provide new thickeners for aqueous surfactant solutions which would be free from the disadvantages described above.

DESCRIPTION OF THE INVENTION

The present invention relates to esters of fatty acids with ethoxylated polyols, which are obtained by:

a) ethoxylating polyols with 80 to 200 moles of ethylene oxide per mole of polyol at elevated temperatures in the presence of basic catalysts and b) subsequently reacting the reaction product with 1 to 1.3 moles of fatty acid per mole of the hydroxyl groups present in the original polyol in the presence of acidic catalysts.

It has surprisingly been found that the esters according to the invention are suitable as particularly effective nitrogen-free thickeners for aqueous surfactant solutions.

Esters having particularly favorable thickening properties are derived from adducts of 90 to 150 moles of ethylene oxide with 1 mole of glycerol which have been esterified with saturated fatty acids containing 12 to 18 carbon atoms.

The present invention also relates to a process for the production of esters of fatty acids with ethoxylated polyols, characterized in that a) polyols are ethoxylated with 80 to 200 moles of ethylene oxide per mole of polyol at elevated temperatures in the presence of basic catalysts and b) the reaction product is subsequently reacted with 1 to 1.3 moles of fatty acid per mole of the hydroxyl groups present in the original polyol in the presence of acidic catalysts.

In the content of the invention, polyols which may be used as starting materials for the esters according to the invention are understood to be substances which have at least three hydroxyl groups. Typical examples are glycerol, diglycerol, triglycerol, oligoglycerols with an average degree of condensation of 4 to 10, trimethylol propane and pentaerythritol. Glycerol is preferably used.

The polyols may be ethoxylated by methods known per se. Suitable basic catalysts for this purpose are, for example, sodium hydroxide, potassium hydroxide, sodium methylate, calcined hydrotalcite [DE 38 43 713 A1] and hydrotalcite hydrophobicized with fatty acids [DE 40 10 606 A1].

The molar ratio of polyol to ethylene oxide may be in the range from 1:80 to 1:200. To obtain esters having particularly advantageous thickening properties, it has proved to be optimal to select a ratio of 1:90 to 1:150 and, more particularly, a ratio of 1:110 to 1:150.

The ethoxylation reaction is carried out under known conditions, i.e. at elevated temperature, for example at a temperature of 120° to 190° C. and preferably 150° to 180° C., and under a pressure of 1 to 5 bar. The addition of the ethylene oxide onto the free hydroxyl groups of the polyols follows the laws of statistics.

After the ethoxylation, the ethoxylated polyols formed as intermediate products are subjected to esterification. The carboxylic acid component used for this purpose is selected from fatty acids corresponding to formula (I):

$$R^1CO\text{—}OH \qquad (I),$$

in which $R^1CO$ is a linear or branched, aliphatic, optionally hydroxy-substituted acyl moiety containing 6 to 22 carbon atoms and 0, 1, 2 or 3 double bonds.

Typical examples are caproic acid, caprylic acid, capric acid, lauric acid, myristic acid, palmitic acid, palmitoleic acid, stearic acid, oleic acid, elaidic acid, petroselic acid, linoleic acid, linolenic acid, ricinoleic acid, 12-hydroxystearic acid, arachic acid, gadoleic acid, behenic acid and erucic acid. Palmitic acid and stearic acid and technical mixtures thereof are preferred.

As usual in oleochemistry, these acids may also be present in the form of the technical cuts obtained in the pressure hydrolysis of natural fats and oils, for example palm oil, palm kernel oil, coconut oil, olive oil, sunflower oil, rapeseed oil or beef tallow. Saturated fatty acids containing 12 to 18 carbon atoms are preferred, those containing 16 to 18 carbon atoms being particularly preferred.

The esterification of the ethoxylated polyols formed as intermediate products with the fatty acids may also be carried out by methods known per se. Suitable acidic catalysts for this purpose are, for example, methanesulfonic acid, butanesulfonic acid, p-toluenesulfonic acid, naphthalenesulfonic acid, alkyl benzenesulfonic acid and/or sulfosuccinic acid.

In addition, it is advisable to carry out the esterification reaction at elevated temperatures, for example at temperatures of 140° to 200° C. and preferably 150° to 170° C. and continuously to remove the water of reaction from the equilibrium. The quantity of fatty acid used should be selected so that there are 1.0 to 1.3 and preferably 1.0 to 1.15 moles of fatty acid for every mole of the hydroxyl groups present in the original polyol. This ensures that the esterification of the hydroxyl groups is substantially quantitative. If desired, a residual content of free fatty acid in the end reaction product may be neutralized with alkali metal hydroxide solution.

When the esters according to the invention are added to aqueous surfactant solutions, a thickening effect is observed and may be enhanced by addition of inorganic electrolyte salts.

Accordingly, the present invention also relates to the use of the esters according to the invention as thickeners for aqueous surfactant solutions, to which they may be added in quantities of 0.1 to 5% by weight and preferably in quantities of 1 to 3% by weight, based on the solids content of the solutions.

Surfactants which may advantageously be thickened in accordance with the present invention are, for example, fatty alcohol sulfates, fatty alcohol ether sulfates, alkanesulfonates, sulfosuccinic acid monoesters and diesters, alkyl phosphates, protein fatty acid condensates, acyl isethionates, acyl taurides, soaps, alkyl ether carboxylic acids, acyl sarcosides, alkyl amidobetaines, imidazolinium betaines or sulfobetaines containing a lipophilic fatty residue with 6 to 22 carbon atoms. Surfactants of which aqueous solutions may be thickened particularly effectively by addition of the esters according to the invention are, on the one hand, fatty alcohol ether sulfates containing 12 to 18 carbon atoms in the fatty alkyl moiety and 1 to 10 ethylene oxide units in the polyether chain and also betaines. Information on the constitution and production of these surfactants can be found in J. Falbe (ed.), *Surfactants in Consumer Products* (Springer Verlag, Berlin, 1986), pages 54 to 85.

The surfactant solutions may have a solids content of 1 to 50% by weight and preferably 5 to 25% by weight, based on the solution.

The surfactant solutions according to the invention may also contain small quantities of fragrances, dyes, opacifiers and pearlescers, antimicrobial agents, preservatives, skin-cosmetic agents, plant extracts, protein hydrolyzates, buffer substances, complexing agents and other known auxiliaries and additives typically encountered in hair shampoos, bath additives, shower bath preparations, liquid soaps, liquid skin-cleansing preparations and also in liquid laundry detergents and dishwashing detergents and liquid household cleaners.

Increasing the viscosity of aqueous solutions of the above-mentioned type with comparatively low surfactant contents is of particular interest from the point of view of practical application. In cases such as these, the addition of the esters according to the invention synergistically improves thickenability with inorganic electrolyte salts.

Suitable inorganic electrolyte salts are any water-soluble alkali metal, ammonium and alkaline earth metal salts, for example the fluorides, chlorides, bromides, sulfates, phosphates, nitrates, providing they am soluble in water at 20° C. in a quantity of at least 1% by weight. The chlorides or sulfates of an alkali metal, ammonium or magnesium are preferably used. Sodium chloride and magnesium chloride are particularly preferred. The inorganic electrolyte salts may be added to the aqueous surfactant solutions in concentrations of 0.1 to 5% by weight and preferably in concentrations of 0.1 to 2% by weight, based on the aqueous solution.

The following Examples are intended to illustrate the invention without limiting it in any way.

EXAMPLES

I. Production Examples

Glycerol-110 EO-tripalmitate/stearate (H1)

a) Ethoxylation:

46.0 g (0.5 mole) of glycerol and 1.6 g (0.03 mole) of potassium hydroxide were introduced into a 5 liter steel autoclave in the form of a 50% by weight aqueous solution. The pressure reactor was then heated to a temperature of 110° C. over a period of 1 h and at the same time evacuated (30 mm Hg). The reaction temperature was then increased to 160° C. and 2420 g (55 moles) of ethylene oxide were continuously introduced under pressure over a period of 2 h, an autogenous pressure of 4 to 5 bar being established. After the ethylene oxide had been added, the mixture was left to react for another 30 minutes. The reaction mixture was then cooled and freed from pressure.

b) Esterification 1000 g (0.15 mole) of glycerol-110 EO-adduct (from a), 126 g (0.47 mole) of tallow fatty acid ($C_{16}:C_{18}=1:1$) and 3 g (0.02 mole) of methanesulfonic acid in the form of a 70% by weight aqueous solution were introduced into a 2 liter three-necked flask equipped with a stirrer and distillation column and heated to 90° C. The reaction mixture was then heated to 160° C. and was stirred at that temperature first for 4 h under a reduced pressure of 30 mm Hg and then for another 12 h at approximately 2 mm Hg, the water of condensation being continuously distilled off from the equilibrium.

Glycerol-130 EO-tripalmitate/stearate (H2)

Production Example H1 was repeated, except that the ethoxylation was carried out with 2860 g (65 moles) of ethylene oxide.

Glycerol-150 EO-tripalmitate/stearate (H3)

Production Example H1 was repeated, except that the ethoxylation was carried out with 3300 g (75 moles) of ethylene oxide.

II. Application Examples

The thickening effect of the esters according to the invention was tested in aqueous solutions of fatty alcohol ether sulfate salts both with and without addition of inorganic electrolyte salts. The viscosity measurements were carried out in a Brookfield RVT viscosimeter (spindle 2–7, 10 r.p.m.). The solids content of the solution was 10% by weight; the temperature was 20° C. The results are set out in Table 1.

Formulation A:

37 g of lauryl alcohol-2.35 EO-sulfate Na salt (Texapon® PN-235, a product of Pulcra S.A, Spain)

2 g of glycerol-110 EO-tripalmitate/stearate (H1)

61 g of water

Formulation B:
- 37 g of lauryl alcohol-2.35 EO-sulfate Na salt (Texapon® PN-235, a product of Pulcra S.A, Spain)
- 2 g of glycerol-130 EO-tripalmitate/stearate (H2)
- 61 g of water Formulation C:
- 37 g of lauryl alcohol-2.35 EO-sulfate Na salt (Texapon® PN-235, a product of Pulcra S.A, Spain)
- 2 g of glycerol-150 EO-tripalmitate/stearate (H3)
- 61 g of water Formulation D:
- 37 g of lauryl alcohol-2.35 EO-sulfate Na salt (Texapon® PN-235, a product of Pulcra S.A, Spain)
- 2 g of polyethylene glycol distearate molecular weight of the polyethylene glycol: approximately 6000 (Eumulgin EO-33, a product of Pulcra S.A., Spain)
- 61 g of water

TABLE 1

Viscosity measurements (in 1000 cPs)

| Ex. | Formulation | \multicolumn{7}{c}{Addition of Sodium Chloride, % by Weight} |
|-----|-------------|---|---|---|---|---|---|---|
|     |             | 0 | 0.5 | 1.0 | 1.5 | 2.0 | 2.5 | 3.0 |
| 1   | A           | 15 | 22 | 42 | 57 | 79 |   | 118 |
| 2   | B           | 20 | 30 | 48 | 61 | 80 |   | 140 |
| 3   | C           | 24 | 40 | 52 | 64 | 82 |   | 160 |
| C1  | D           |    |    |    | 1  | 9  | 38 | 82 |

The invention claimed is:

1. Esters of fatty acids with ethoxylated polyols obtainable by:
   (a) ethoxylating polyols with 110 to 200 moles of ethylene oxide per mole of polyol at elevated temperatures in the presence of basic catalysts and
   (b) subsequently reacting product of the ethoxylating of step (a) with 1 to 1.3 moles of fatty acid per mole of the hydroxyl groups present in the original polyol in the presence of acidic catalysts.

2. Esters as claimed in claim 1, wherein the polyols are selected from the group consisting of glycerol, diglycerol, triglycerol, oligoglycerols with an average degree of condensation of 4 to 10, trimethylol propane and pentaerythritol.

3. Esters as claimed in claim 2, wherein the fatty acids correspond to formula (I):

$$R^1CO-OH \qquad (I),$$

in which $R^1CO$ is a linear or branched, aliphatic, optionally hydroxy-substituted acyl moiety containing 6 to 22 carbon atoms and 0, 1, 2 or 3 double bonds.

4. Esters of fatty acids with ethoxylated polyols that are made by a process wherein:
   (a) polyols are ethoxylated with 100 to 200 moles of ethylene oxide per mole of polyol at elevated temperatures in the presence of basic catalysts and
   (b) the reaction product is subsequently reacted with 1 to 1.3 moles of fatty acid per mole of the hydroxyl groups present in the original polyol in the presence of acidic catalysts.

5. Esters as claimed in claim 4, wherein the polyols reacted are selected from the group consisting of glycerol, diglycerol, triglycerol, oligoglycerols with an average degree of condensation of 4 to 10, trimethylol propane and pentaerythritol.

6. Esters as claimed in claim 5, that are made by a process wherein basic catalysts selected from the group consisting of sodium hydroxide, potassium hydroxide, sodium methylate, calcined hydrotalcite and hydrotalcite hydrophobicized with fatty acids are used for ethoxylation.

7. Esters as claimed in claim 6, that are made by a process wherein ethoxylation is carried out at a temperature of 120° to 190° C.

8. Esters as claimed in claim 7, that are made by a process wherein ethoxylation is carried out under a pressure of 1 to 5 bar.

9. Esters as claimed in claim 8, wherein the fatty acids reacted correspond to formula (I):

$$R^1CO-OH \qquad (I),$$

in which $R^1CO$ is a linear or branched, aliphatic, optionally hydroxy-substituted acyl moiety containing 6 to 22 carbon atoms and 0, 1, 2 or 3 double bonds.

10. Esters as claimed in claim 9, that are made by a process wherein acidic catalysts selected from the group consisting of methanesulfonic acid, butanesulfonic acid, p-toluenesulfonic acid, naphthalenesulfonic acid, alkyl benzenesulfonic acid and sulfosuccinic acid are used for esterification.

11. Esters as claimed in claim 10, that are made by a process wherein esterification is carried out at temperatures of 140° to 200° C.

12. A process for thickening aqueous solutions of surfactants, wherein the improvement comprises use of esters as claimed in claim 1 as thickeners.

13. A process for thickening aqueous solutions of surfactants, wherein the improvement comprises use of the esters claimed in claim 4 as thickeners.

14. Esters as claimed in claim 1, wherein the fatty acids correspond to formula (I):

$$R^1CO-OH \qquad (I),$$

in which $R^1CO$ is a linear or branched, aliphatic, optionally hydroxy-substituted acyl moiety containing 6 to 22 carbon atoms and 0, 1, 2 or 3 double bonds.

15. Esters as claimed in claim 4 that are made by a process wherein basic catalysts selected from the group consisting of sodium hydroxide, potassium hydroxide, sodium methylate, calcined hydrotalcite and hydrotalcite hydrophobicized with fatty acids are used for ethoxylation.

16. Esters as claimed in claim 4 that ate made by a process wherein ethoxylation is carried out at a temperature of 120° to 190° C.

17. Esters as claimed in claim 4 that are made by a process wherein ethoxylation is carried out under a pressure of 1 to 5 bar.

18. Esters as claimed in claim 4, wherein the fatty acids reacted correspond to formula (I):

$$R^1CO-OH \qquad (I),$$

in which $R^1CO$ is a linear or branched, aliphatic, optionally hydroxy-substituted acyl moiety containing 6 to 22 carbon atoms and 0, 1, 2 or 3 double bonds.

19. Esters as claimed in claim 4 that are made by a process wherein acidic catalysts selected from the group consisting of methanesulfonic acid, butanesulfonic acid, p-toluenesulfonic acid, naphthalenesulfonic acid, alkyl benzenesulfonic acid and sulfosuccinic acid are used for esterification.

20. Esters as claimed in claim 4 that are made by a process wherein esterification is carried out at temperatures of 140° to 200° C.

* * * * *